United States Patent
Imaizumi et al.

(10) Patent No.: US 6,792,161 B1
(45) Date of Patent: Sep. 14, 2004

(54) IMAGE INPUT DEVICE WITH DUST DETECTOR

(75) Inventors: Shoji Imaizumi, Shinshiro (JP); Keisuke Hashimoto, Toyokawa (JP)

(73) Assignee: Minolta Co., Ltd., Osaka (JP)

( * ) Notice: Subject to any disclaimer, the term of this patent is extended or adjusted under 35 U.S.C. 154(b) by 0 days.

(21) Appl. No.: 09/363,055

(22) Filed: Jul. 29, 1999

(30) Foreign Application Priority Data

Jul. 31, 1998 (JP) .......................................... 10-217124

(51) Int. Cl.⁷ .......................... G01N 21/88; G06K 9/40
(52) U.S. Cl. .................... 382/275; 358/463; 356/237.1; 356/237.2; 356/237.5
(58) Field of Search ................................ 382/275, 254; 358/463, 474, 497, 483, 3.26; 356/237.1, 239.1, 239.2, 239.3, 124, 237.2, 237.5, 954; 359/216

(56) References Cited

U.S. PATENT DOCUMENTS

| | | | |
|---|---|---|---|
| 4,747,647 A | * 5/1988 | de Zoeten et al. | 359/216 |
| 4,769,532 A | * 9/1988 | Kawakami | 250/205 |
| 4,933,983 A | * 6/1990 | Hiramatsu et al. | 382/112 |
| 5,250,969 A | * 10/1993 | Abe et al. | 396/382 |
| 5,436,979 A | * 7/1995 | Gray et al. | 382/141 |
| 5,446,586 A | * 8/1995 | Dornier | 359/507 |
| 5,499,114 A | * 3/1996 | Compton | 358/483 |
| 5,907,398 A | * 5/1999 | Fujino et al. | 356/237.3 |
| 5,982,948 A | * 11/1999 | Shimada et al. | 382/274 |
| 6,035,072 A | * 3/2000 | Read | 382/275 |
| 6,292,269 B1 | * 9/2001 | Kawai | 358/1.9 |
| 6,320,679 B1 | * 11/2001 | Noda et al. | 358/473 |

FOREIGN PATENT DOCUMENTS

| | | | | |
|---|---|---|---|---|
| GB | 1547811 | * | 4/1976 | H04N/3/36 |
| GB | 1547812 | * | 4/1976 | H04B/3/36 |
| JP | 60154769 | * | 8/1985 | H04N/1/04 |
| JP | 2000078355 | * | 1/1988 | H04N/1/04 |
| JP | 07092109 | * | 9/1993 | G01N/21/90 |
| JP | 06-006589 | | 1/1994 | |
| JP | 06-022133 | | 1/1994 | |
| JP | 07-177314 | | 7/1995 | |
| JP | 09149217 | * | 6/1997 | H04N/1/19 |
| JP | 2000078355 | * | 9/1998 | H04N/1/04 |
| JP | 10-294870 | | 11/1998 | |
| JP | 2001102799 A | * | 4/2001 | H05K/13/08 |

* cited by examiner

Primary Examiner—Kimberly A. Williams
Assistant Examiner—Melanie Vida
(74) Attorney, Agent, or Firm—Morrison & Foerster LLP

(57) ABSTRACT

An image input device identifies what part of the optical input system needs cleaning when there is dust or other foreign matter in the optical input system. This image input device has an image noise position detector for capturing image data from a scanner, and detecting the main scanning address of noise information corresponding to image noise present in the image data; a focus calculator for calculating focus information around the main scanning address detected by the image noise position detector; focus information storage for storing focus information for each sub-scanning line; and a foreign matter position determining circuit for determining the location of foreign matter on the scanner based on the focus information stored in the focus information storage.

17 Claims, 11 Drawing Sheets

IMAGE INPUT DEVICE WITH DUST DETECTOR

This application is based on application No. 10-217124 filed in Japan, the contents of which is hereby incorporated by reference.

BACKGROUND OF THE INVENTION

1. Field of the Invention

The present invention relates to an image input device for generating a digital image signal by scanning a document, and relates more specifically to an image input device for detecting dust or other foreign matter on the optical input system for optically scanning a document.

2. Description of the Prior Art

Image input devices, such as image scanners and the scanning unit of a photocopying machine, whereby a CPU reads captured shading data and determines whether picture elements detected by a CCD sensor are normal picture elements or abnormal picture elements are known from the literature. See, for example, Japanese Patent Laid-Open Publication No. 6-6589.

Conventional image scanners for reading shading data and detecting normal and abnormal picture elements can also detect dust or other foreign matter on the shading panel. They are, however, unable to detect such dust or other foreign matter on the CCD sensor, the lens, and other parts of the optical input system. They are also unable to determine where the dust or other foreign matter is located.

SUMMARY OF THE INVENTION

It is therefore an object of the present invention to provide an image input device capable of determining a cleaning position when dust or other foreign matter is in the optical input system.

In addition to the above, it is a further object of the present invention to provide an image input device for informing the user of the position needing cleaning, that is, the cleaning position, when dust or other foreign matter is in the optical input system.

To achieve the above objects, an image input device according to the present invention comprises a scanning means for scanning a document image; an image noise position detector for capturing image data output from the scanning means, and detecting the main scanning address of noise information corresponding to image noise present in the image data; a focus calculating means for calculating focus information around the main scanning address detected by the image noise position detector; focus information storage for storing the focus information for each subscanning line; and foreign matter position determining means for determining the location of foreign matter on the scanning means based on the focus information stored in the focus information storage.

An image input device thus comprised according to the present invention first detects the main scanning address of any noise information corresponding to image noise in the image data, and then calculates focus information for the image elements in the area of the noise information. This focus information is stored for each subscanning line and used to determine the location of any dust or other foreign matter in the scanning means. It is therefore possible to know that there is dust in the input optics and where this dust is located. This makes it possible to reliably remove a cause of image noise in the output image, and thereby obtain a clear output image.

The scanning means preferably has a document platen glass on which an original document is placed; a light source for emitting light to scan an original document placed on the document glass while moving relative to the original document; a mirror for guiding reflected light from the original document to a lens system; a lens system for imaging light reflected thereto by the mirror on a photoelectric conversion element; and a photoelectric conversion element for outputting image data.

In this case, the foreign matter position determining means determines that foreign matter is present on the photoelectric conversion element or document platen glass if the focus calculating means determines that image focus is good; that foreign matter is on the photoelectric conversion element if focus is good and the foreign matter data width is large; that foreign matter is on the mirror or lens if focus is not good; and that foreign matter is on the mirror if focus is not good and there is a change in the focus information in the subscanning direction.

It will thus be obvious that an image input device according to the present invention can determine where dust or other foreign matter is present in the optical input system, that is, on the document platen glass, mirror, lens system, or photoelectric conversion element, based on the calculated focus information. It is therefore possible to detect where on what element of the optical input system dust or other foreign matter is present, and it is therefore possible to easily remove the dust or other foreign matter. The location of dust or other foreign matter in the optical input system can therefore also be displayed on an operating panel, for example, so that a user can easily know where the dust or other foreign matter is located on what part of the optical input system. Cleaning is thus made easier.

An image input device according to the present invention thus further preferably comprises a cleaning position indicating means for informing a user of the result detected by the foreign matter position determining means.

Other objects and attainments together with a fuller understanding of the invention will become apparent and appreciated by referring to the following description and claims taken in conjunction with the accompanying drawings.

DESCRIPTION OF THE PREFERRED EMBODIMENTS

The preferred embodiments of the present invention are described below with reference to the accompanying figures wherein an image input device according to the present invention is shown and described as applied in a digital color photocopying machine, referred to hereafter as simply a photocopying machine.

It is to be further noted that "dust" as used below refers to dust and any other type of foreign matter that not desirably present in the imaging system. Overall configuration of the photocopying machine.

Figure 1:
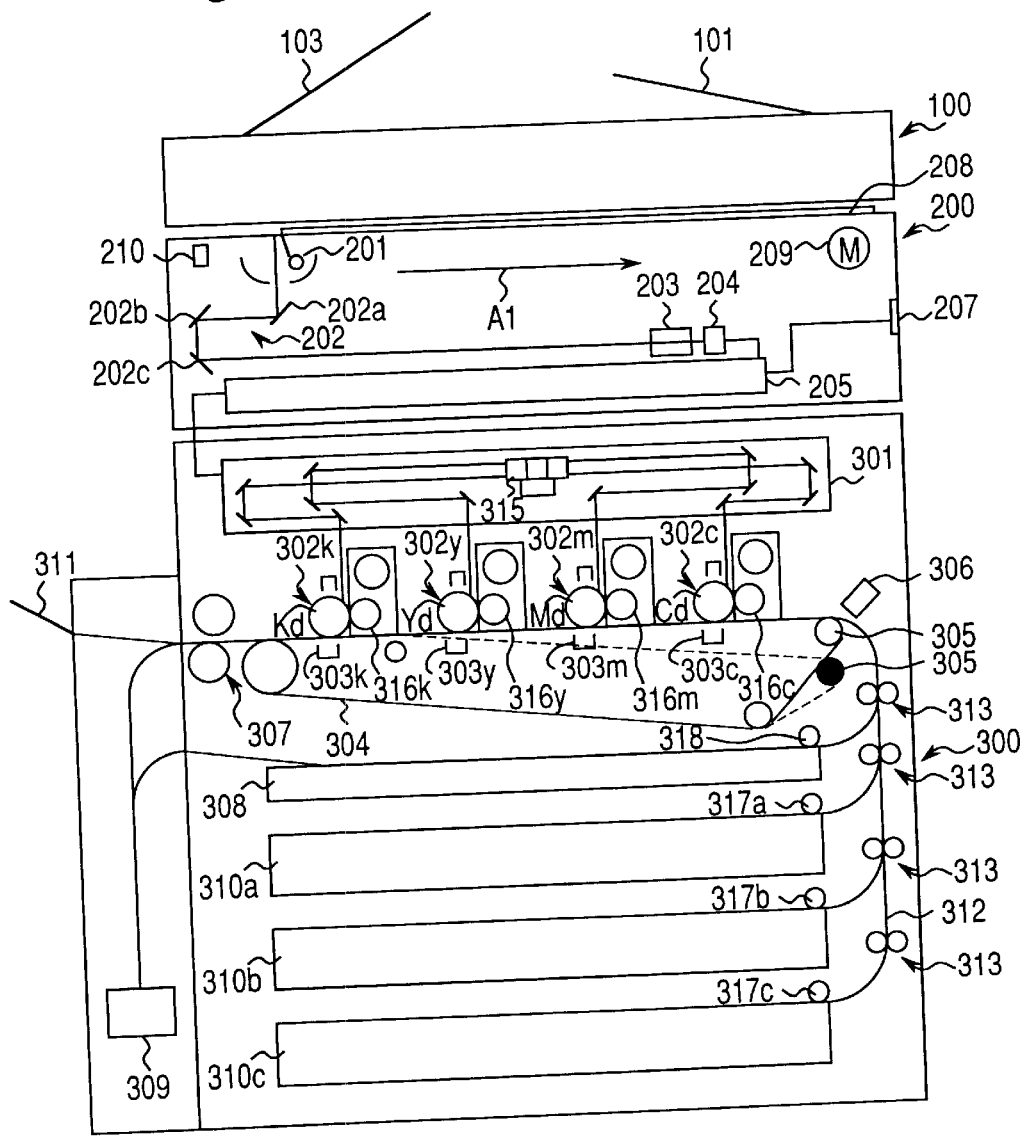
FIG. 1 is an overall view of a digital color photocopying machine comprising an image input device according to the present invention.

As shown in FIG. 1, a photocopying machine 90 comprises an automatic document feeder (ADF) 100, image scanner 200, and image printer 300. In a photocopying machine 90 thus comprised, the ADF 100 automatically transports an original document placed in the ADF 100 to a predetermined image scanning position at which the image scanner 200 scans and captures an image of the document. The captured image data is then sent to the image printer 300 whereby a copy of the original document is reproduced on paper or other recording medium.

When provided with an appropriate interface circuit 207, this type of photocopying machine 90 can also be connected to a personal computer or other external device (not shown in the figures). This interface circuit 207 thus enables the photocopying machine 90 to output image data captured by the image scanner 200 to an external device, and also enables an external device to send image data to the image printer 300 of the photocopying machine 90 for printing.

The ADF 100, image scanner 200, and image printer 300 are described more specifically below.

(a) ADF 100

The ADF 100 transports an original document placed in the document tray 101 to the image scanning position of the image scanner 200, and then ejects the scanned document to the eject tray 103. Transporting a document to the scanning position is controlled according to commands entered from the operating panel 211 (see FIG. 2) on the image scanner 200; transporting scanned documents to the eject tray 103 is performed according to a scanning end signal from the image scanner 200. When a plurality of original documents is placed on the document tray 101, these control signals are applied in controlled succession so that the document transport, scanning, and eject operations are efficiently performed.

(b) Image Scanner 200

When exposure lamp 201 of the image scanner 200 emits light to an original document on the platen glass 208, a mirror group 202 comprising first, second, and third mirrors 202a, 202b, and 202c directs light reflected from the original document to lens 203, and thus forms an image on CCD sensor 204. The exposure lamp 201 and first mirror 202a form a scanner, which is driven by scanner motor 209 at a speed V determined by the copy magnitude in the direction of arrow A1. The scanner scans the full width of the document placed on the platen glass 208. The second mirror 202b and third mirror 202c also move at speed V/2 in the same direction and in conjunction with the movement of exposure lamp 201 and first mirror 202a. The scanner motor 209 is controlled by the CPU 2056 of the image processing circuit 205 (see FIG. 2).

The position of the scanner, which is below assumed to comprise exposure lamp 201 and first mirror 202a, expressed as the distance moved from the home position is calculated and controlled based on the output from the scanner home position sensor 210 and the step count of the scanner motor 209.

Reflected light from a document that is incident to the CCD sensor 204 is converted to an image signal by the CCD sensor 204. This image signal is processed by the image processing circuit 205, which is described further in detail below, and then sent to the interface circuit 207 and image printer 300. Processing by the image processing circuit 205 includes analog processes such as signal amplifying, A/D conversion, and digital image processing.

(c) Image Printer 300

The image printer 300 converts the image data received from the image scanner 200 or interface circuit 207 to cyan (C), magenta (M), yellow (Y), and black (K) print data, and sends this print data to the print head 301. The print head 301 drives a separate laser according to the image signals for each of the four print data colors (CMYK) for primary scanning by means of polygonal mirror 315, thereby exposing photoconductors Cd, Md, Yd, and Kd in the imaging units 302c, 302m, 302y, and 302k.

Photoconductors Cd, Md, Yd, and Kd and other elements required to complete an electrophotographic process are disposed inside each of the imaging units 302c, 302m, 302y, and 302k. The photoconductors Cd, Md, Yd, and Kd turn clockwise as seen in FIG. 1 so that imaging processes are successively completed for each color. The imaging units 302c, 302m, 302y, and 302k required for this imaging operation are integrated for each color process, and can be separately installed to the photocopying machine 90.

Latent images on the photoconductors Cd, Md, Yd, and Kd in the imaging units 302c, 302m, 302y, and 302k are then developed by color developers 316c, 316m, 316y, and 316k. A transfer charger 303c, 303m, 303y, and 303k is disposed opposite each of the photoconductors Cd, Md, Yd, and Kd inside the loop of a paper transportation belt 304. As the copy paper or other recording medium is transported by the paper transportation belt 304 between each photoconductor and corresponding transfer charger, the toner image developed on each of the photoconductors Cd, Md, Yd, and Kd is transferred to the paper.

The paper to which the latent images are transferred is supplied in the following sequence to the image transfer position for toner image formation. The paper cassettes 310a, 310b, and 310c in this exemplary photocopying machine can each hold a different size of paper. A paper feed roller 317a, 317b, and 317c is also disposed to each cassette 310a, 310b, and 310c. When a particular paper size is selected, the feed roller 317 for the corresponding cassette 310 picks a sheet and supplies it to the transportation path 312. Paper supplied to the transportation path 312 is fed by transport roller pairs 313 to the paper transportation belt 304. A timing sensor 306 detects a reference mark on the paper transportation belt 304 to control the transport timing of the supplied form.

Each of the imaging units 302c, 302m, 302y, and 302k also has an internal resist compensation sensor (not shown in the figures) for preventing offset colors caused by a resist shift. This is accomplished by detecting the reference mark on the paper transportation belt 304 to fine adjust the image data supply timing as required.

The transferred toner image is then heated and melted by the fixing roller pair 307 to fuse and fix the image on the paper. The finished copy is then ejected to the eject tray 311.

When a duplex copy is made, the form is inverted by form inversion unit 309 after the first-side image is fixed by the fixing roller pair 307. The inverted form is then guided by the duplex unit 308 so that feed roller 318 reintroduces the form to the transportation path 312. The above-described printing process is then repeated to print to the second side, after which the duplex copy is deposited to the eject tray 311.

It is to be noted that belt retraction roller 305 can be operated to retract the paper transportation belt 304 from the path of imaging units 302c, 302m, and 302y. This makes it possible to prevent contact between the paper transportation belt 304 and the CMY imaging units 302c, 302m, and 302y when making a monochrome, that is, black and white, copy. By thus stopping the CMY imaging units 302c, 302m, and 302y from being driven, unnecessary wear of the photoconductors Cd, Md, and Yd and related process components can be reduced.

Image Processing Circuit

Figure 2:
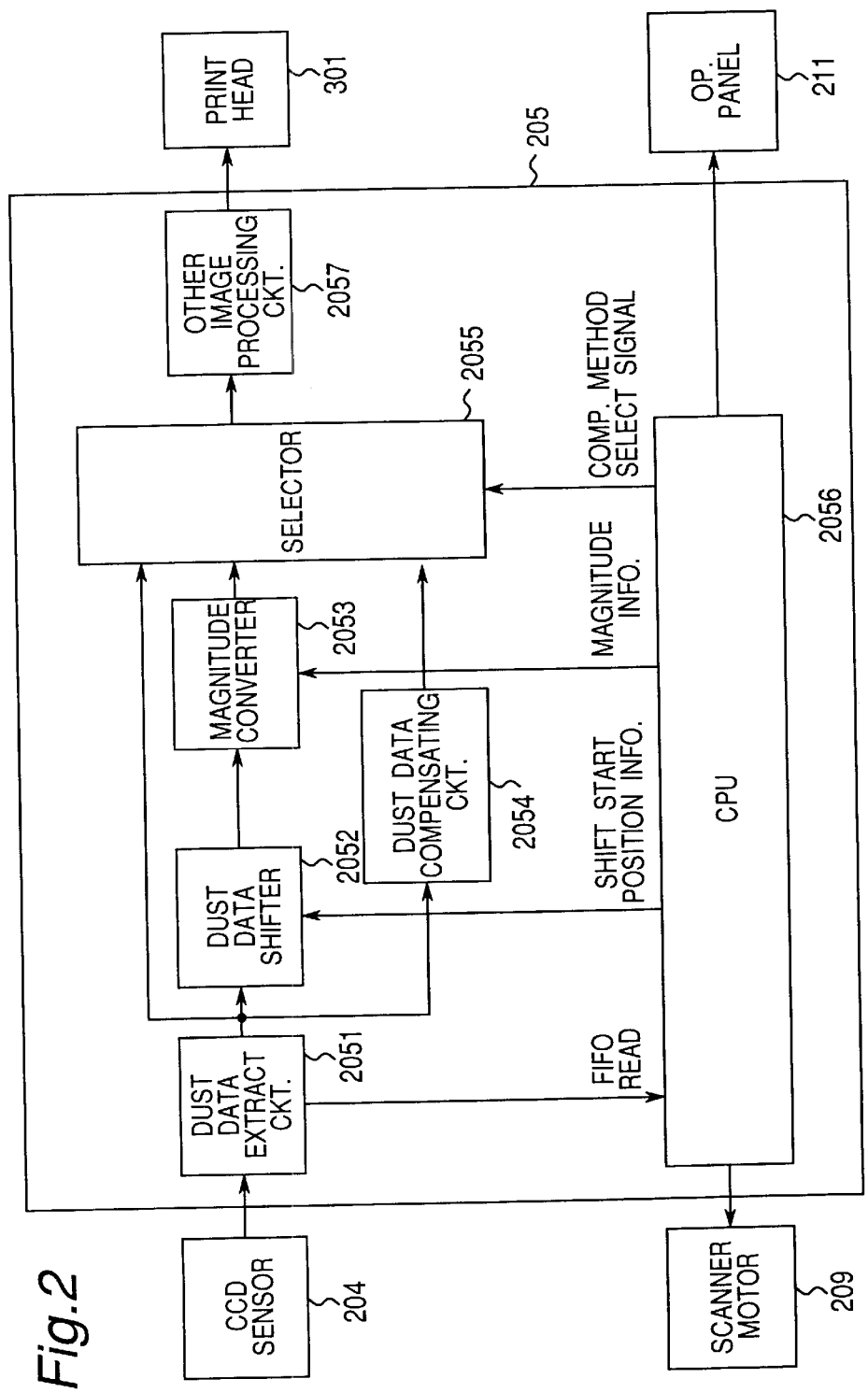
FIG. 2 is a block diagram of an image processing circuit.

FIG. 2 is a block diagram of the image processing circuit 205. As shown in FIG. 2, this image processing circuit 205 comprises a dust data extracting circuit 2051, a dust data shifter 2052, magnitude converter 2053, dust data compensating circuit 2054, selector 2055, CPU 2056, and other image processes circuit 2057.

The dust data extracting circuit 2051 detects whether dust or other foreign matter is present (detects dust presence), the dust position in the main scanning direction, and the dust width, based on the image data supplied from the CCD sensor 204. As will be described in further detail below, the dust data extracting circuit 2051 performs a particular process to the image data and then stores the processed image data to a FIFO (first-in, first-out) buffer. The CPU 2056 then reads data from the FIFO buffer to detect the above-noted dust-related information. Based on the dust position and dust width data extracted by the dust data extracting circuit 2051 in the main scanning direction, the dust data shifter 2052 then shifts the image data to force dropping image data where dust is detected in the output image.

The magnitude converter 2053 then enlarges the image data to compensate for image reduction in the main scanning direction as a result of pixel dropping in the main scanning direction by the dust data shifter 2052. The image data enlargement magnitude is determined by the CPU 2056 based on the dust width information extracted in the main scanning direction by the dust data extracting circuit 2051. It will thus be obvious that as dust size increases, so does the enlargement magnitude used by the magnitude converter 2053. The dust data compensating circuit 2054 compensates for image data lost because of dust or other foreign matter by means of an interpolation process calculating the lost information from the surrounding information.

Based on the data extracted by the dust data extracting circuit 2051, the selector 2055 selects the image data passed to the other image processes circuit 2057. More specifically, the selector 2055 is controlled by the CPU 2056 to select the output from the magnitude converter 2053, the dust data compensating circuit 2054, or the dust data extracting circuit 2051. The other image processes circuit 2057 applies image processing operations other than the dust detection and removal process described above, and outputs the result of those image processes to the print head 301. The image processes performed by the other image processes circuit 2057 typically include, for example, MTF compensation and color conversion operations.

The dust data extracting circuit 2051, dust data shifter 2052, and dust data compensating circuit 2054 of the image processing circuit 205 shown in FIG. 2 are described in further detail below with reference to FIG. 3 to FIG. 8.

(a) Dust Data Extracting Circuit 2051

Figure 3:
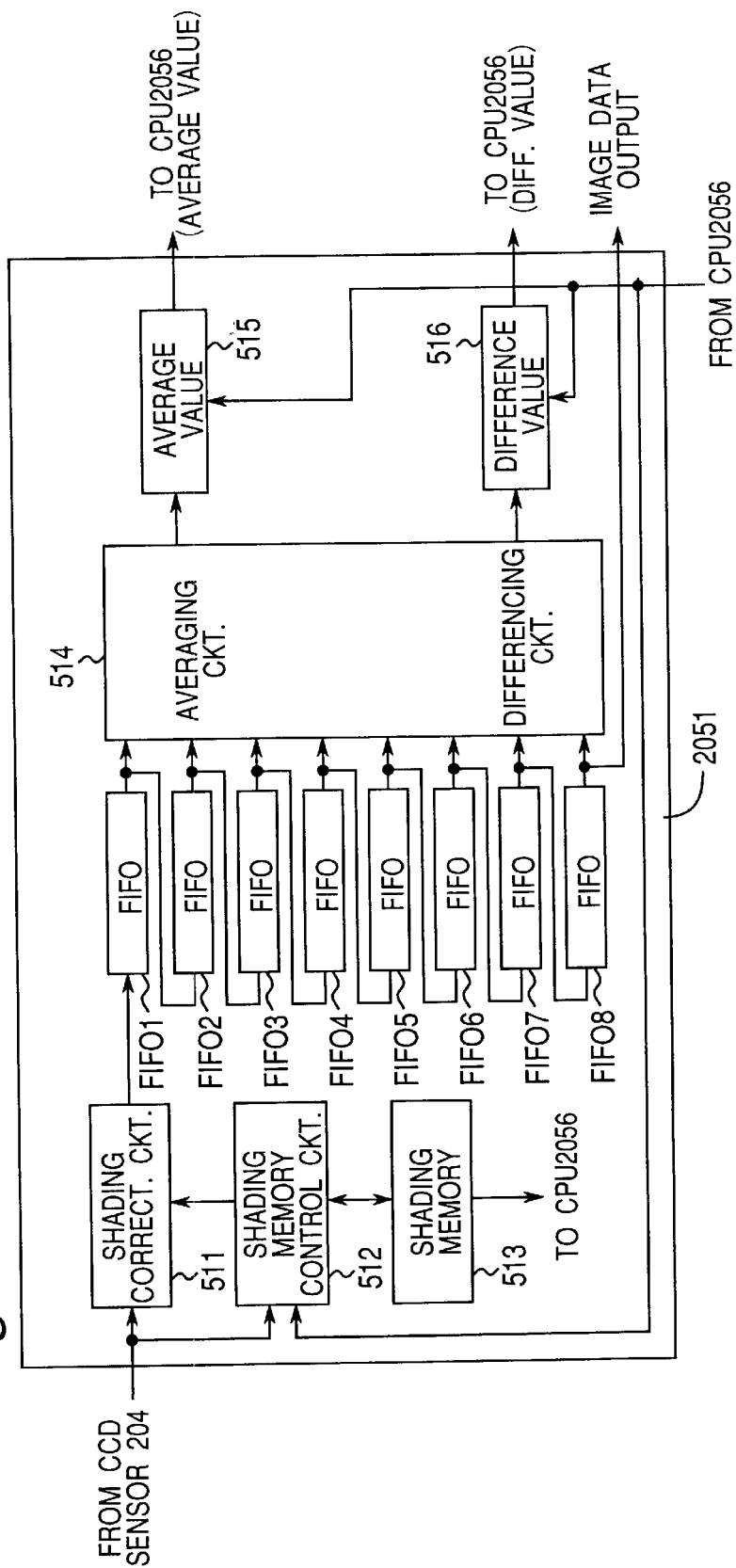
FIG. 3 is a block diagram of a foreign matter data extracting circuit in the image processing circuit shown in FIG. 2.

The dust data extracting circuit 2051 of the image processing circuit 205 is shown in FIG. 3. As shown in FIG. 3, this dust data extracting circuit 2051 comprises a shading correction circuit 511, shading memory controller 512, shading memory 513, FIFO buffer 1 to FIFO buffer 8, averaging and differencing circuit 514, average value memory 515, and difference value memory 516. Image data from the CCD sensor 204 is supplied directly to the shading correction circuit 511 and shading memory controller 512.

The shading correction circuit 511 compensates for variations in CCD sensor sensitivity resulting from production differences in the CCD sensor 204 chip. When there is dust or other foreign matter on the shading plate, CCD sensor 204, first to third mirrors 202a to 202c, or lens 203, light does not pass to the CCD sensor 204 at the pixel(s) where the dust or other foreign matter is present, and there is a resulting drop in the shading data signal level compared with where there is no dust when the shading correction circuit 511 thus compensates for variations in sensitivity.

The result of this operation is written by the shading memory controller 512 to the shading memory 513, and can be accessed therefrom by the CPU 2056 (see FIG. 2). That is, the CPU 2056 can detect problems in the shading data by reading data from the shading memory 513, and can thereby identify the position and width of dust or other foreign matter in the shaded image data along the main scanning direction.

The shading memory controller 512 stores plural lines of sensitivity corrected image data in the subscanning direction to FIFO buffers 1 to 8. Note that in this exemplary embodiment eight lines are stored.

For each pixel in the main scanning direction, the averaging and differencing circuit 514 calculates the average ((maximum+minimum)/2) and the difference (maximum−minimum) in the subscanning direction based on the data stored to FIFO buffers 1 to 8. The results are stored to average value memory 515 and difference value memory 516, which can be read and written by the CPU 2056 (see FIG. 2).

That is, the CPU 2056 can learn the average ((maximum+minimum)/2) and the difference (maximum−minimum) values for each pixel in the main scanning direction calculated for a plurality of lines in the subscanning direction by simply reading values from the average value memory 515 and difference value memory 516. Based on this information, the CPU 2056 can then detect abnormal pixel values in the scanned image data.

Using a method such as described below, CPU 2056 can therefore detect problems in image shading based on scanned shading data by detecting abnormal pixel values in the scanned image data from the information stored to the average value memory 515 and difference value memory 516.

Figure 4:
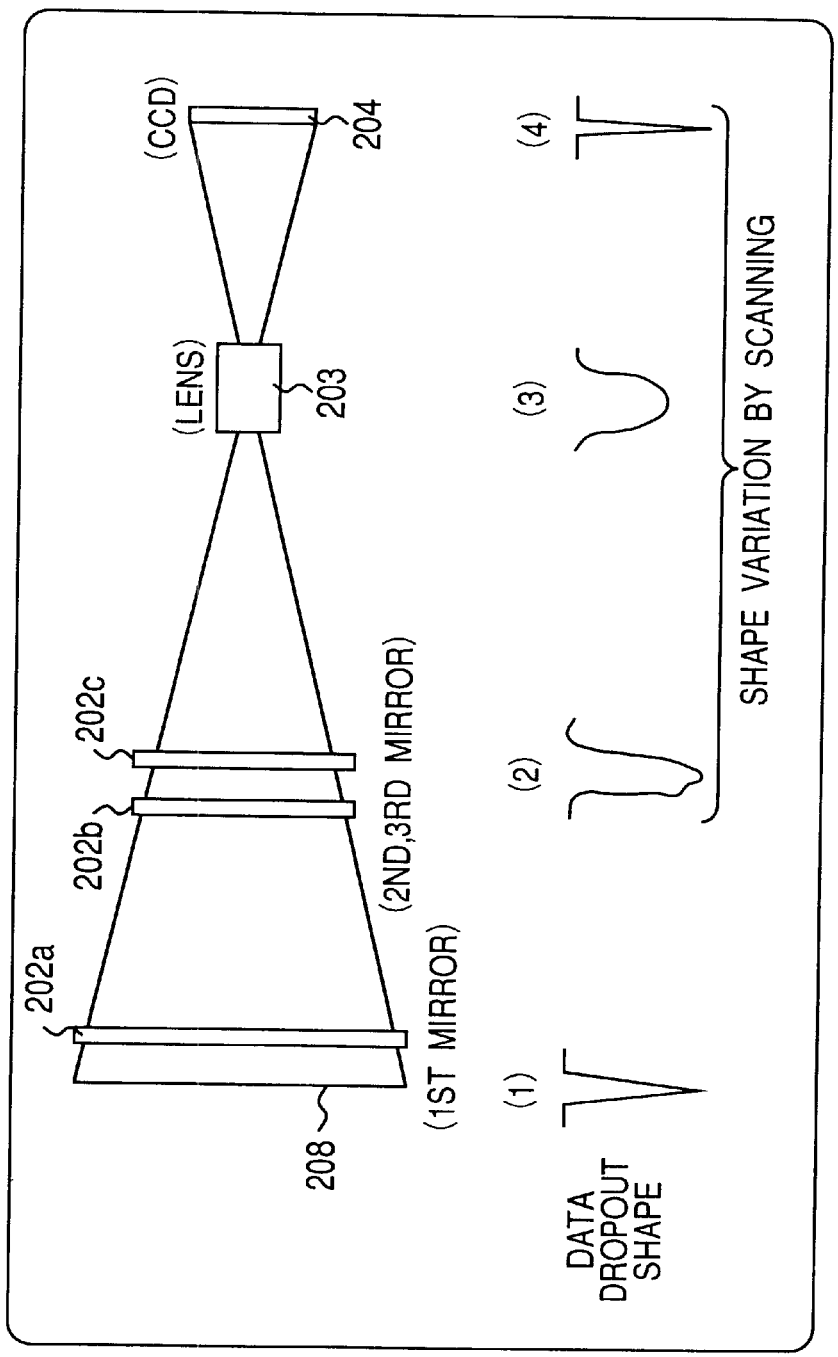
FIG. 4 is used to describe the operation of the foreign matter data extracting circuit shown in FIG. 3.

In the following description the optical path from the platen glass 208 of photocopying machine 90 to the CCD sensor 204 in FIG. 1 is assumed to be configured as shown in FIG. 4. If there is dust on the platen glass 208 or CCD sensor 204 in this case, the dust will be optically in focus. The image data lost in the main scanning direction due to dust on the platen glass 208 or CCD sensor 204 will therefore be sharply defined (see data dropout shape (1) in FIG. 4). Furthermore, assuming dust or other foreign matter of a particular size, dust on the platen glass 208 will optically appear small, while dust on the CCD sensor 204 will appear optically large. It is therefore possible to detect from the size of detected dust whether it is on the platen glass 208 or on the CCD sensor 204.

Furthermore, if the dust or other foreign matter is on the first, second, or third mirror 202a, 202b, or 202c or the lens 203, it will not be in focus. As a result, image data lost in the main scanning direction due to dust on one of the mirrors 202a to 202c or the lens 203 will therefore not be sharply defined. The scanned outline of lost image data will also vary depending upon whether the dust is on the first, second, or third mirror 202a, 202b, or 202c (see FIG. 4 (2) to (4)). This is because the distance between lens 203 and first to third mirrors 202a to 202c changes during scanning. If the image data dropout shape is not sharply defined, it is therefore possible to control the scanner motor 209 and monitor data dropout at plural positions to estimate where the dust or other foreign matter is located.

Figure 5:
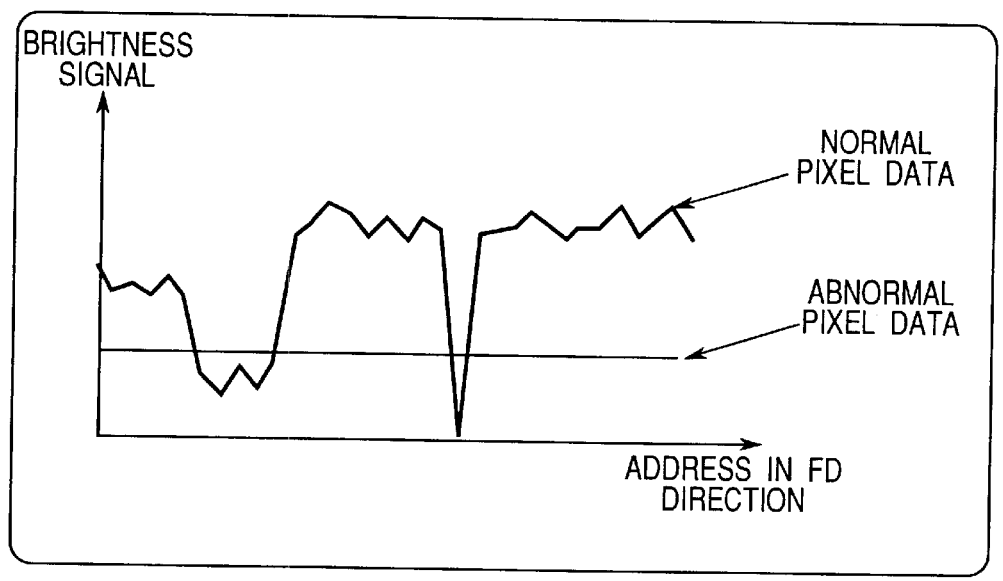
FIG. 5 is used to describe an alternative operation of the foreign matter data extracting circuit shown in FIG. 3.

In normal image data when there is no dust or other foreign matter present, the image density distribution in the subscanning direction will produce abrupt changes in the image data at specific pixels in the main scanning direction. FIG. 5 shows the change in data in the subscanning direction at a particular pixel in the main scanning direction.

Abnormal pixel data resulting from dust or other foreign matter will have little value change in the subscanning direction because incidence on the particular pixel in the main scanning direction is limited, and the luminance signal will therefore be held at a low (high density) level. The CPU 2056 can detect this by monitoring the values written to average value memory 515 and difference value memory 516.

(b) Dust Data Shifter 2052

Figure 6:
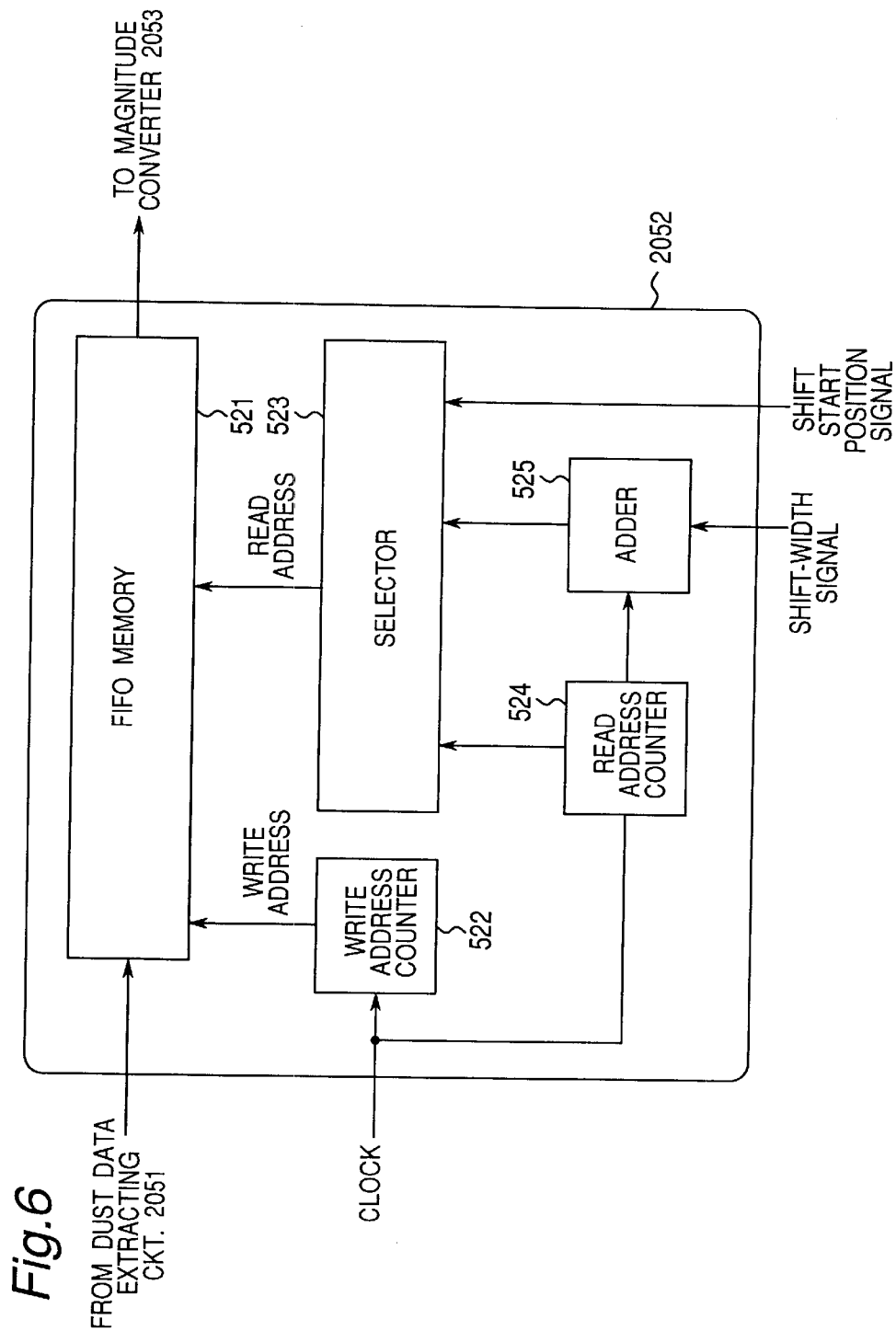
FIG. 6 is a block diagram of a foreign matter data shift circuit in the image processing circuit shown in FIG. 2.
Figure 7:
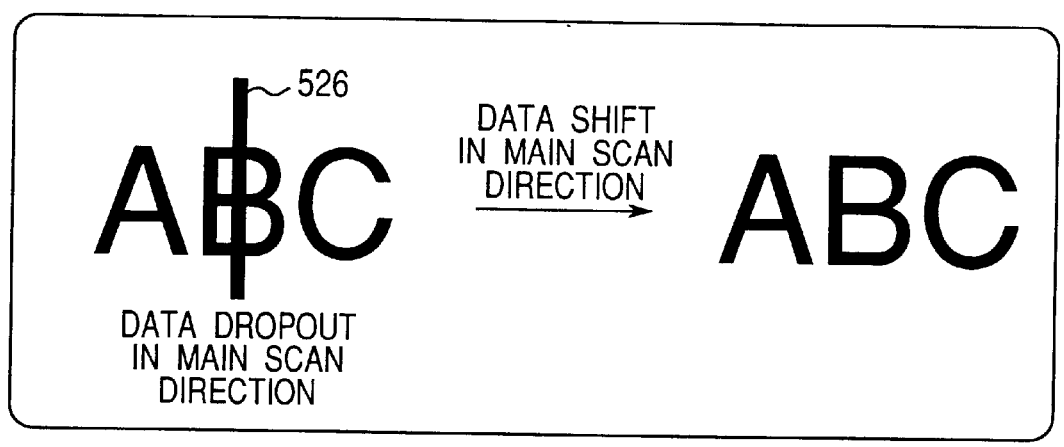
FIG. 7 is used to describe the operation of the foreign matter data shift circuit shown in FIG. 6.

Based on the dust position and dust width information extracted in the main scanning direction by the dust data extracting circuit 2051, the dust data shifter 2052 shifts the image data to drop image data where dust is detected as noted above. The dust data shifter 2052 of the image processing circuit 205 shown in FIG. 2 is shown in FIG. 6.

This exemplary dust data shifter 2052 comprises FIFO buffer 521, write address counter 522, selector 523, read address counter 524, and adder 525. The read address of the FIFO buffer 521 in the dust data shifter 2052 is controlled according to the shift start address signal and the shift width signal applied from the CPU 2056 shown in FIG. 2.

The read address counter 524 increments the read address synchronized to the clock. The adder 525 shifts the address from the read address counter 524 by adding an address equivalent to the data width (shift width) supplied from the CPU 2056 to the address from the read address counter 524. As a result, the read address from the FIFO buffer 521 is forced to skip image data of a specific width, thereby dropping the image data stored to the skipped addresses.

The selector 523 switches the address supplied to the FIFO buffer 521, and therefore the output therefrom, between the address passed from the read address counter 524 and the address calculated by the adder 525. The address selection, that is, selector 523 operation, is controlled by the shift start address signal from the CPU 2056 such that FIFO buffer 521 reading progresses according to the address from the read address counter 524 until the specified shift start address is reached, and then shifts to the address from the adder 525 at the shift start address.

Using a dust data shifter 2052 thus comprised, a black line 526 in the subscanning direction produced by dust can be forcibly dropped by shifting data in the main scanning direction, thereby achieving a cleaner, easier to read image.

(c) Dust Data Compensating Circuit 2054

Figure 8:
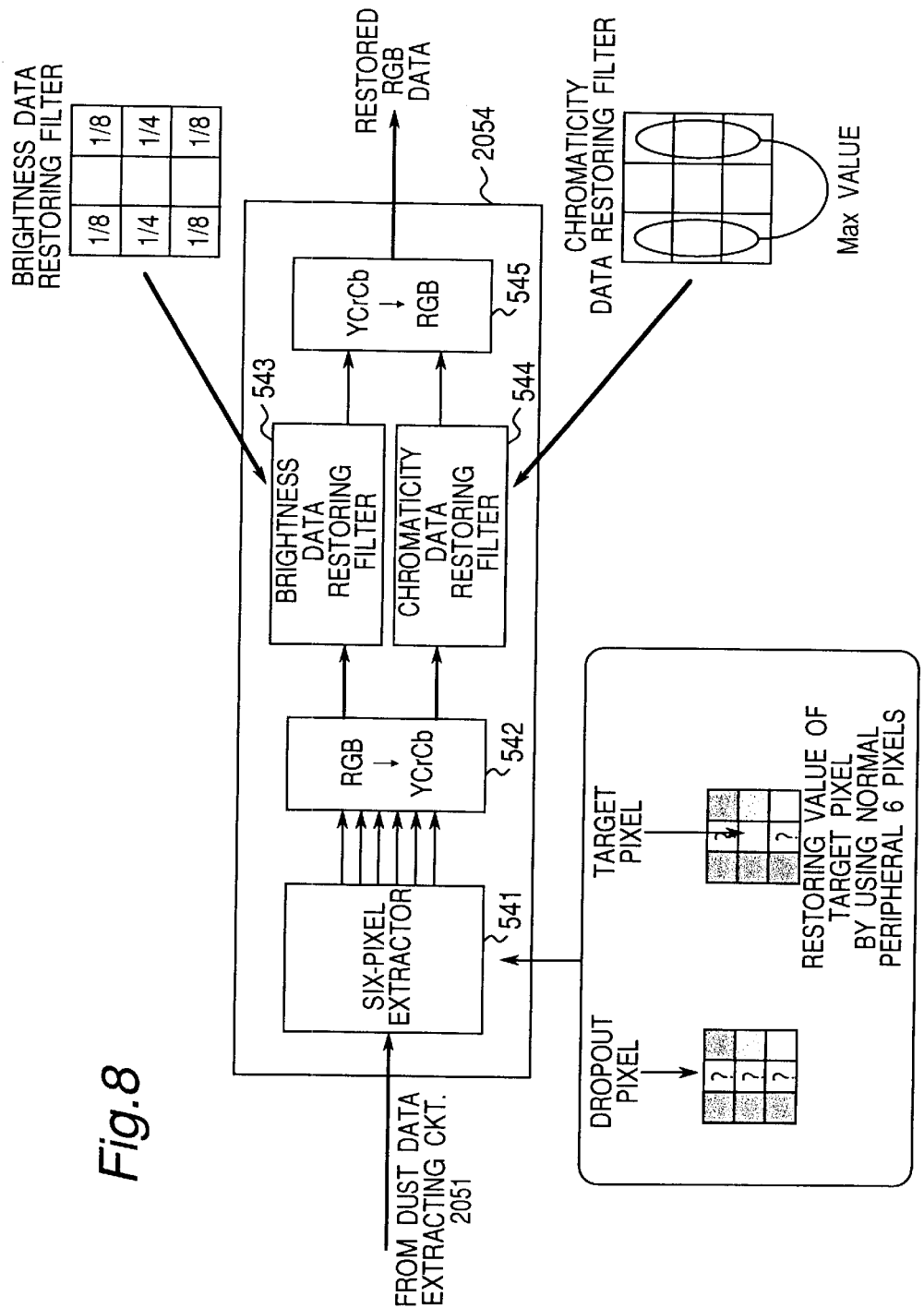
FIG. 8 is a block diagram of a foreign matter data compensation circuit.

An exemplary dust data compensating circuit 2054 in the image processing circuit 205 shown in FIG. 2 is described next with reference to FIG. 8. As shown in FIG. 8, this dust data compensating circuit 2054 comprises a six-pixel extractor 541, a color space conversion circuit 542, brightness data restoring filter 543, chromaticity data restoring filtering 544, and reconversion circuit 545. The color space conversion circuit 542 converts image data from an RGB color space to a YCrCb (brightness, chromaticity) color space. The reconversion circuit 545 then reconverts the image data from the YCrCb color space to an RGB color space.

The six-pixel extractor 541 extracts a 3×3 pixel block around the image data dropout line in the main scanning direction resulting from dust or other foreign matter, and then extracts the six pixels not including the three pixel dropout line. Based on these six pixels, the color space conversion circuit 542 converts the image data from an RGB color space to a YCrCb (brightness, chromaticity) color space. Note that this color space conversion requires different restoration filtering methods for brightness and chromaticity information.

The brightness data restoring filter 543 determines the restored image brightness by calculating the value of the center pixel based on the six pixel values extracted by the six-pixel extractor 541. In this exemplary embodiment, the brightness data restoring filter 543 determines the center pixel value by calculating for all pixels the sum of ¼ of the horizontally adjacent pixel values and ⅛ of the diagonally adjacent pixel values. Note that it will be obvious to one with ordinary skill in the related art that various other methods can be alternatively used.

The chromaticity data restoring filtering 544 determines the restored chromaticity value by calculating the value of the center pixel based on the six pixel values extracted by the six-pixel extractor 541. In this exemplary embodiment, the chromaticity data restoring filtering 544 determines the center pixel value by detecting the maximum chromaticity value of all six adjacent pixels. Note that it will be obvious to one with ordinary skill in the related art that various other methods can be alternatively used.

The compensated image data is then converted by the reconversion circuit 545 from a YCrCb color space to RGB color space.

By applying different data restoration methods for brightness and chromaticity data, an image input device according to the present invention can reproduce sharp text images with minimal color bleeding, as well as smooth color transitions in photographic images, for example. Control Process The main control loop of the CPU 2056 is described next below. Note that this main control loop includes a foreign matter detection process and a foreign matter location detection process as subroutines, which are also described below.

(a) Main Control Loop

Figure 9:
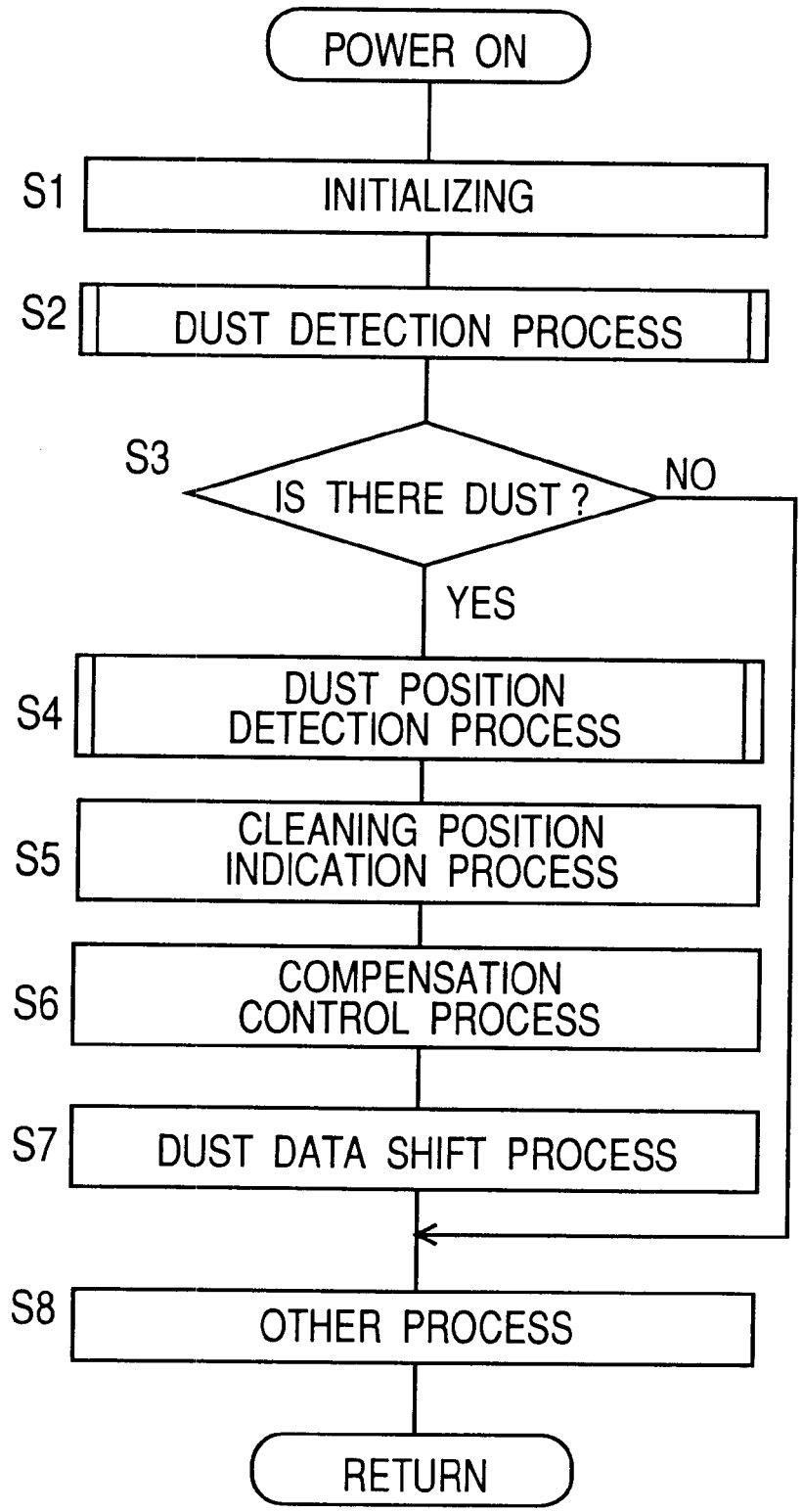
FIG. 9 is a flow chart of the main control loop of an image processing circuit according to the present invention.

FIG. 9 is a flow chart of the main control loop of an image processing circuit according to the present invention. When the power is turned on and this control loop starts, various parameters and other settings required for image processing and photocopying machine 90 control are initialized (S1). Dust or other foreign matter in the copying system will also cause image noise in the copied image. Before copying begins, it is therefore necessary to perform the foreign matter detection process and evaluate the results thereof to determine whether there is any dust or other foreign matter present (S2 and S3).

If decision diamond S3 determines there is dust or other foreign matter (yes), the location of the dust is detected in S4, and the user is then informed (S5) of the location needing cleaning by presenting appropriate indication on the operating panel 211 (FIG. 2). Based on the result of the foreign matter location detection process (S4), a compensation control process determines what method of dust compensation to apply (S6). In this preferred embodiment, if the dust width is detected to be only one pixel, the dust data compensating circuit 2054 is used for image data compensation; otherwise the dust data shifter 2052 is used. The selector 2055 is driven to control which method is used.

A dust data shift process as described above is then performed in S7 to determine where data shifting starts and how far to shift the image data based on the result of the foreign matter detection process.

If foreign matter is not detected (S3 returns no), the selector 2055 passes image data without using the dust data compensating circuit 2054 or dust data shifter 2052.

Copying, printing, or other processes are performed after steps S1 to S7 (S8), and the main loop then returns.

(b) Foreign Matter Detection Process

Figure 10:
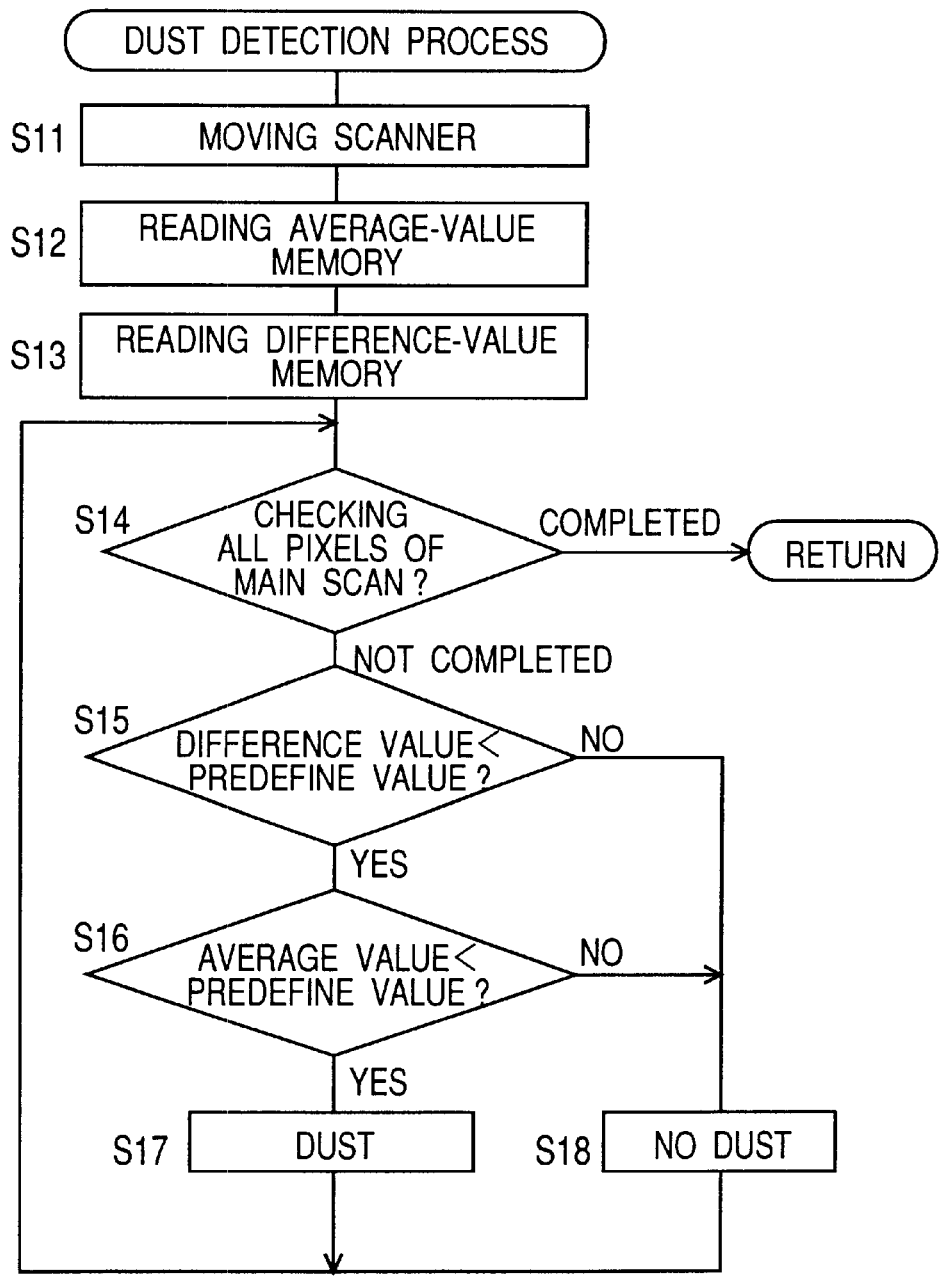
FIG. 10 is a flow chart of the foreign matter detection process shown in FIG. 9.

The foreign matter detection process S2 is shown in FIG. 10.

When this process starts, the scanner motor 209 is driven to scan and capture image data for a plurality of lines in the subscanning direction. The CPU 2056 then reads the average and difference values from the average value memory 515 and difference value memory 516 of the dust data extracting circuit 2051 (S12 and S13).

Steps S14 to S16 are then sequentially processed to detect whether all pixels have been checked in the main scanning direction, and whether the values from the average value memory 515 or difference value memory 516 are less than predefined threshold values. If all pixels in the main scanning direction have not been checked (S14 returns "incomplete"), and both average and difference value conditions are met (S15 and S16 both return yes), there is dust or other foreign matter present (S17).

If not all pixels have been checked and either S15 or S16 returns no, there is no dust or other foreign matter present (S18). This loop is repeated until S14 determines that all pixels in the main scanning direction have been processed and checked. It is therefore possible to identify at what main scanning address dust or other foreign matter is present.

It should be noted that the reliability of the dust detection process can be improved by repeating the above process multiple times, and determining dust or other foreign matter to be present only when it has been detected plural times at the same main scanning address.

(c) Foreign Matter Location Detection Process S4

Figure 11:
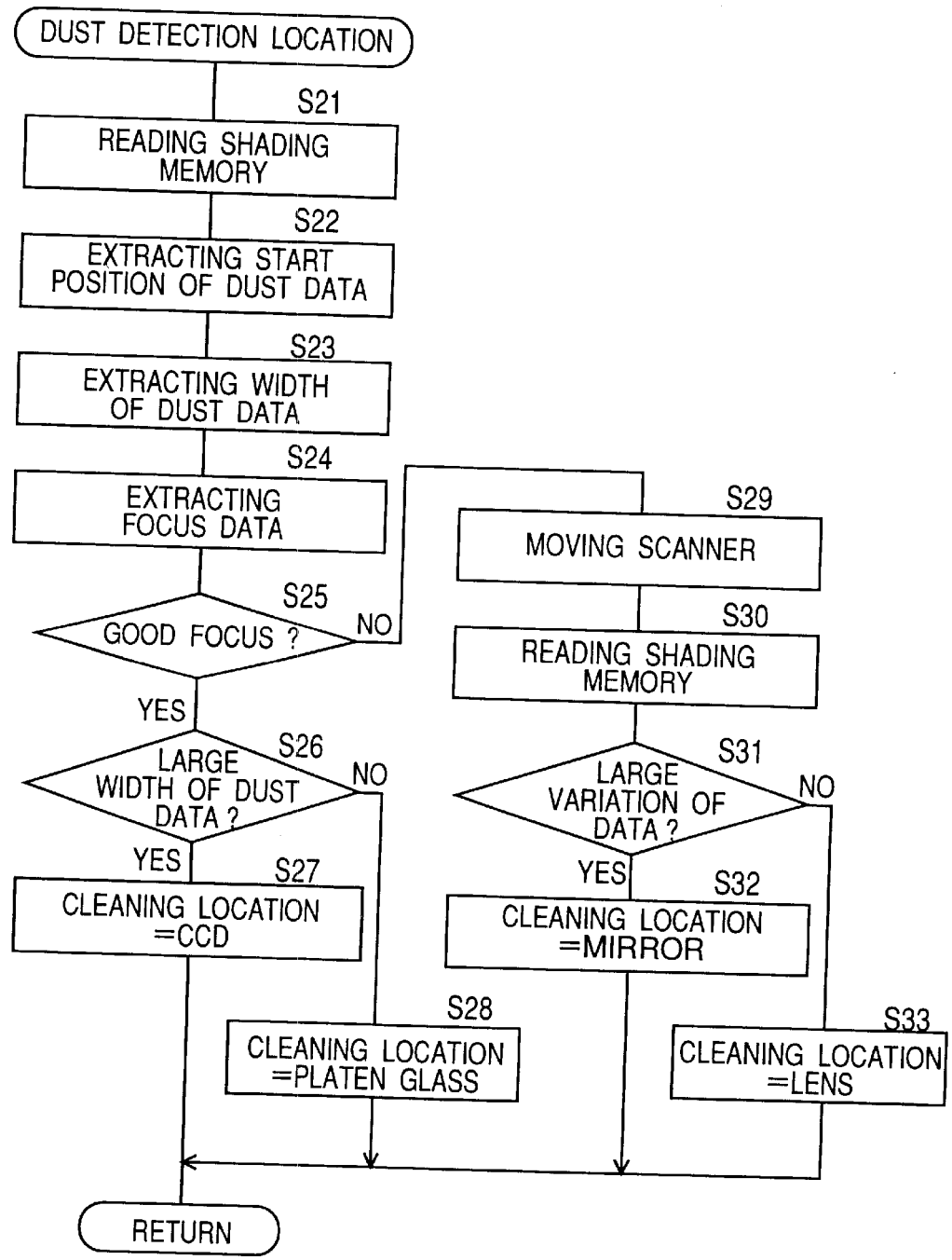
FIG. 11 is a flow chart of the foreign matter location detection process shown in FIG. 9.

The foreign matter location detection process S4 is shown in FIG. 11.

When this process starts, the CPU 2056 reads data from the shading memory 513 (S21), detects the dust data starting position (S22), and detects the dust width (S23) Note that the shading data usually has a high luminance value because the shading panel is read. Shading data where there is dust, however, has a luminance value below a specific threshold value, and shading data below this threshold luminance value can therefore be detected as dust or other foreign matter.

Focus information is then extracted by monitoring data around the suspected dust spot, and the difference of adjacent pixels is calculated (S24). Decision diamond 25 determines focus to be good when the calculated difference exceeds a particular threshold value, that is, when the difference is high.

If focus is good, the dust data width is examined. That is, decision diamond S26 determines whether the data width exceeds a particular position. If it does (yes), the cleaning position is determined to be near the CCD sensor 204 (S27); if not (S26 returns no), the cleaning position is near the platen glass 208 (S28).

If focus is not good (S25 returns no), the scanner is moved (S29), and the shading memory is read again (S30). The change between the current scanned data and the last data scanned is then calculated. If the change is great (S31 returns yes), the cleaning position is determined to be in the area of the first to third mirrors 202a to 202c (S32); if not (S31 returns no), the cleaning position is in the area of the lens 203 (S33).

It is therefore possible to detect the approximate location of any dust or other foreign matter by analyzing image data focus and the detected width of the dust candidate, as well as the change in image data as the scanner position changes.

Although the present invention has been described in connection with the preferred embodiments thereof with reference to the accompanying drawings, it is to be noted that various changes and modifications will be apparent to those skilled in the art. Such changes and modifications are to be understood as included within the scope of the present invention as defined by the appended claims, unless they depart therefrom.

What is claimed is:

1. An image input device comprising:
   an optical system projecting an image to be captured;
   a sensor capturing the image projected thereon by the optical system and disposed in an optical path of the optical system, said sensor comprising a plurality of picture elements;
   a first controller detecting noise in an image signal outputted from the sensor and identifying one of the picture elements of the sensor corresponding to the noise; and
   a second controller identifying in the optical path a location of a substance causing the noise detected by the first controller.

2. The image input device as set forth in claim 1, wherein the second controller detects focus information of the projected image at the picture element identified by the first controller, and identifies the location of the substance based on the focus information.

3. The image input device as set forth in claim 2, wherein the focus information relates to a difference between an image signal level of the picture element and the image signal level of a picture element located around the picture element.

4. The image input device as set forth in claim 1, further comprising an indication device indicating the position identified by the second controller.

5. The image input device as set forth in claim 1, further comprising a computation device removing the noise from the image signal.

6. An image input device comprising:
   a sensor having a plurality of picture elements arranged in a main scanning direction;
   an optical system for projecting onto the sensor an image to be scanned,
      said optical system moving in a subscanning direction orthogonal to the main scanning direction to sequentially project the image onto the picture elements of the sensor, and
      comprising a plurality of optical elements configured so that a distance between the optical elements changes as the optical system moves in the subscanning direction;
   a first controller detecting noise in an image signal outputted from the sensor and identifying a picture element of the sensor corresponding to the noise; and a second controller identifying one of the optical elements which has a substance causing the noise based on a change in image signal outputted from the identified picture element when the optical system moves in the subscanning direction.

7. The image input device as set forth in claim 6, wherein the optical elements include a mirror that moves in conjunction with a subscanning operation and a lens that is stationary during the subscanning operation, and the second controller determines that the substance is present on the mirror when a change in the noise is large, and determines that the substance is present on the lens when the change is small.

8. The image input device as set forth in claim 6, further comprising an indication device indicating the optical element identified by the second controller.

9. The image input device as set forth in claim 6, further comprising a computation device removing the noise.

10. A detection method for detecting a location of a substance disposed in an optical system, said method comprising:

projecting an optical image onto a sensor by the optical system;

capturing the projected optical image by the sensor;

detecting noise due to the substance in an output signal from the sensor based on the captured optical image;

identifying one of picture elements of the sensor corresponding to the noise; and determining a location in an optical path of the optical system of the substance causing the noise.

11. The detection method as set forth in claim 10, wherein the determining comprises detecting focus information of the projected optical image at the identified picture element, and identifying the location of the substance in the optical path based on the focus information.

12. The detection method as set forth in claim 11, wherein the optical system comprises a plurality of optical elements configured to move relative to each other in the projecting;

the capturing is repeated a plurality of times while the optical elements are moving; and the determining comprises identifying one of the optical that has the substance causing the noise based on a change in the noise while the optical elements are moving.

13. The detection method as set forth in claim 12, wherein the optical elements include a mirror that moves and a lens that is stationary, and the determining further comprises determining that the substance is present on the mirror when the change in the noise is large, and determining that the substance is present on the lens when the change in the noise is small.

14. A detection method for detecting a location of disposed in an image input device, said method comprising:

projecting an optical image onto a sensor by an optical system through an intervening glass for holding an original document;

capturing the projected optical image by the sensor;

detecting noise due to the substance in an output signal from the sensor based on the captured optical image;

identifying one of picture elements of the sensor corresponding to the noise; and determining a location in an optical path of the optical system of the substance causing the noise.

15. The detection method as set forth in claim 14, wherein the determining comprises:

detecting focus information of the projected optical image at the identified picture element, detecting the number of the picture elements of the sensor identified as corresponding to the noise when the detected focus information indicates a good focus, and determining that the substance is on the sensor when the detected number is large, and determining that the substance is on the intervening glass when the detected number is small.

16. The detection method as set forth in claim 15, wherein the optical system comprises a plurality of optical elements configured to move relative manner relative to each other in the projecting;

the capturing is repeated a plurality of times while the optical elements are moving; and the determining comprises identifying one of the optical elements that has the substance causing the noise based on a change in the noise while the optical elements are moving when the focus information does not indicate the good focus.

17. The detection method as set forth in claim 16, wherein the optical elements include a mirror that moves and a lens that is stationary, and the optical element identifying comprises determining that the substance is present on the mirror when the change in the nose is large, and determining that the substrate is present on the lens when the change in the noise is small.

* * * * *